United States Patent
Neuberger et al.

(10) Patent No.: US 6,454,790 B1
(45) Date of Patent: Sep. 24, 2002

(54) TREATMENT FOR BARRETT'S SYNDROME

(75) Inventors: Wolfgang Neuberger, Labuan (MY); Patrice Thierry, Nantes (FR)

(73) Assignee: CeramOptec Industries, Inc., East Longmeadow, MA (US)

( * ) Notice: Subject to any disclaimer, the term of this patent is extended or adjusted under 35 U.S.C. 154(b) by 51 days.

(21) Appl. No.: 09/621,802

(22) Filed: Jul. 21, 2000

(51) Int. Cl.⁷ ................................................. A61N 5/06
(52) U.S. Cl. ................ 607/88; 604/101.04; 604/101.05
(58) Field of Search ............................ 604/36–38, 516, 604/101.04, 101.05; 607/88, 90, 94

(56) References Cited

U.S. PATENT DOCUMENTS

| | | | |
|---|---|---|---|
| 4,146,019 A | * 3/1979 | Bass et al. | 600/108 |
| 4,474,752 A | 10/1984 | Haslam et al. | |
| 4,474,753 A | 10/1984 | Haslam et al. | |
| 4,478,822 A | 10/1984 | Haslam et al. | |
| 5,020,539 A | * 6/1991 | Yokoi et al. | 600/101 |
| 5,314,409 A | * 5/1994 | Sarosiek et al. | 604/101.03 |
| 5,665,064 A | * 9/1997 | Bodicky et al. | 600/156 |
| 5,705,518 A | * 1/1998 | Richter et al. | 514/185 |
| 5,707,355 A | * 1/1998 | Zimmon | 604/104 |
| 5,709,657 A | * 1/1998 | Zimmon | 604/101.05 |
| 5,871,467 A | * 2/1999 | Reuning et al. | 604/264 |
| 5,955,490 A | * 9/1999 | Kennedy et al. | 424/9.61 |
| 6,027,499 A | 2/2000 | Johnson et al. | |
| 6,034,267 A | * 3/2000 | Gierskcky et al. | 424/9.6 |
| 6,086,558 A | * 7/2000 | Bower et al. | 604/20 |
| 6,162,242 A | * 12/2000 | Peyman | 128/898 |
| 6,316,007 B1 | * 11/2001 | Nordquist et al. | 424/184.1 |

* cited by examiner

*Primary Examiner*—Linda C. M. Dvorak
*Assistant Examiner*—H M. Johnson, III
(74) *Attorney, Agent, or Firm*—Bolesh J. Skutnik; BJ Associates

(57) ABSTRACT

An apparatus and method for treating Barrett's tissue by removal of the mucosa through PhotoDynamic Therapy (PDT) is provided. A viscous gel is the medium used to carry the photosensitizer to the treatment site and allow sufficient time to transfer to the tissue. The gel's viscosity will allow it to adhere to the tissue for a sufficient amount of time to transfer the photosensitizer or sufficient time for a mechanical device such as an expanding balloon to press the gel into the tissue. The photosensitizer within the gel is activated by the corresponding wavelength of radiation. An extended multi-balloon system limits the area of treatment and localizes the spread of the gel. An endoscope with fiber optics may be used to view the operation. A preferred embodiment of the apparatus contains a catheter with at least two balloons, one to block drainage of the photosensitizer into the stomach and one to limit the height of the treatment area and to press the gel into the tissue. Included in this embodiment is a tube for the delivery of the gel, a tube for cooling purposes or aspiration, an image bundle and a diffuse light source. The apparatus and method may be used to treat various other diseases involving the gastrointestinal diseases of the mucosa. The most salient feature of this invention is the multi-balloon system used to limit the area of treatment, but effect the entire desired area at one time.

4 Claims, 1 Drawing Sheet

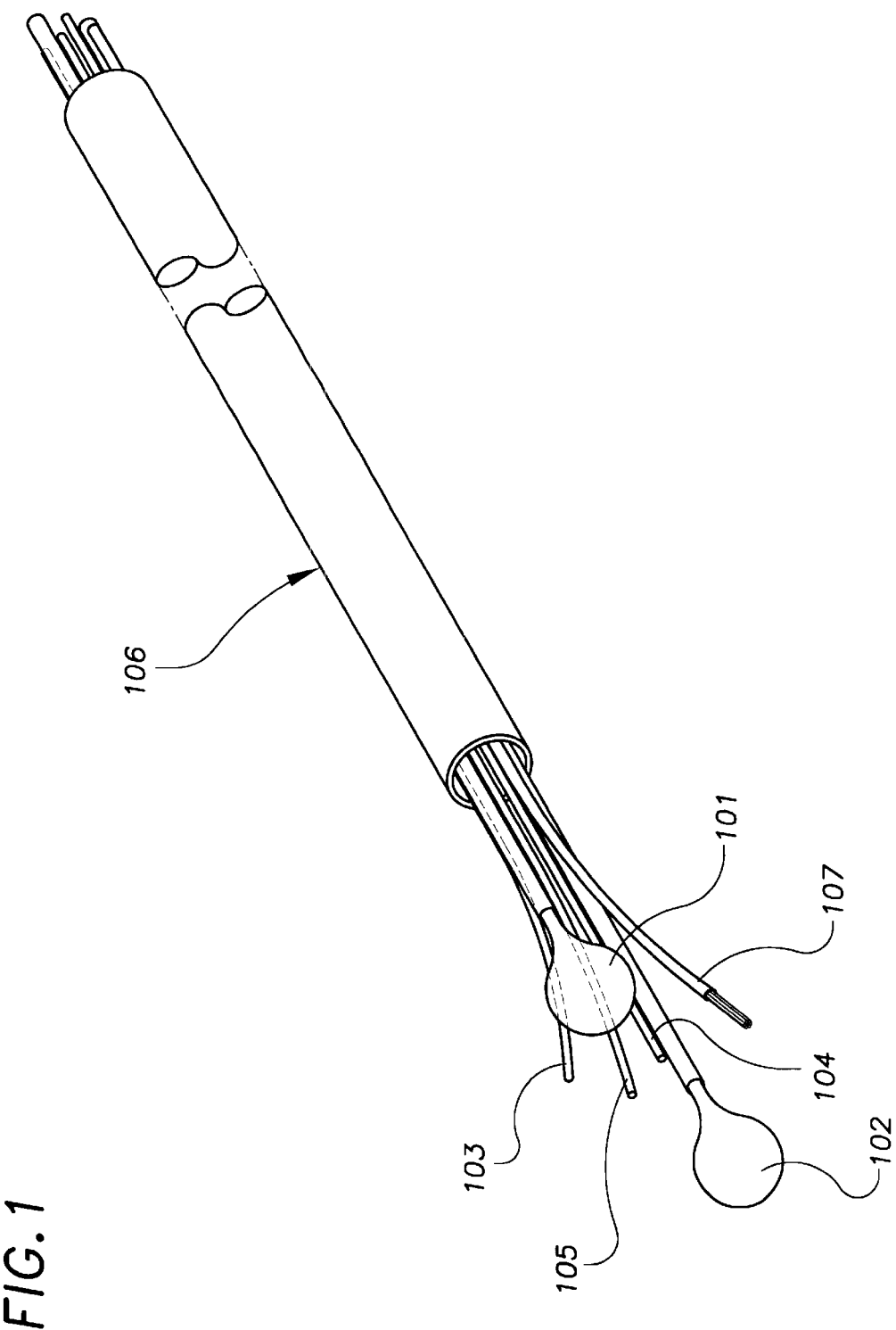

TREATMENT FOR BARRETT'S SYNDROME

BACKGROUND OF THE INVENTION

1. Field of the invention

The present invention relates to the apparatus and method for necrotizing of the interior lining of an organ and more particularly for Barrett's tissue and other lesions of the gastrointestinal tract by PhotoDynamic Therapy (PDT) of the gastrointestinal mucosa (gastrointestinal tract lining).

2. Invention Disclosure Statement

The current state of the art for the treatment of Barrett's syndrome uses a Nd:YAG laser to treat the afflicted areas. (Ertan et al, Am. J. Gastro. 90:2201–2203[1995]). This method uses a 2.2-mm diameter beam ablate the afflicted tissue. With such a narrow beam as compared to the size of the area being treated, the treatment procedure becomes time consuming and laborious. Often the patient will have to undergo multiple procedures for a complete treatment. Also to achieve ablation of tissue, a laser with significant power must be used. This increased power creates a larger potential for damage to the healthy tissue underneath. This method does not reveal how to treat a larger area more quickly, efficiently and more safely.

One method of treating a larger area is demonstrated in U.S. Pat. No. 6,027,499. This method uses nitrogen gas to quickly freeze the afflicted areas. Gas by its nature expands to fill the volume exposed. This expansion increases the area exposed to treatment. The freezing then kills the cells contacted. However, this method is limited by the lack of depth control in the treating of the tissue. Freezing depth is difficult to control. It would be useful to have fine control on the layer of treatment, so as not to damage the unaffected non-cancerous cells in the intima of the esophagus.

Gels have been used to transfer medicines at a controlled rate or to insure transfer through a tissue of the medicine. (e.g. U.S. Pat. Nos. 4,474,752; 4,474,753; 4,478,822).

U.S. Pat. No. 4,474,752 utilizes a thermosetting gel, which gels at body temperature after injection into soft tissue. This liquid is injected into soft tissue where it gels. The gel state releases medication at a measured pace and remains in the injected area until dissolved by the body. The purpose of this invention was to create a slow release subcutaneous mechanism for medication without the discomfort of hard capsules. This invention does not reveal how to deliver medication internally to a site for sole treatment of that site.

U.S. Pat. No. 4,474,753, also utilizes a gel which solidifies on contact with the skin. This gel delivers medicine transdermally while it is attached to the skin. This is also a delivery system for medication for general release, not a site specific medication. It would be useful for a gel to release medication for a specific site.

U.S. Pat. No. 4,478,822 utilizes another gel system to be injected into body cavities for dose sparing purposes. This again is a general release mechanism designed for a prolonged period of controlled drug release. The medicines released are not meant just for the area where the gel has been injected.

It would be useful to have the capability to affect a broad area of treatment during the application of PDT, which will quickly necrotize only the afflicted area and efficiently use the photosensitizer. It would be further useful to have a delivery system for medication to affect one area or system of a body. The present invention addresses these problems.

BRIEF SUMMARY OF THE INVENTION

It is an object of the present invention to provide a treatment for Barrett's Syndrome using the application of photosynthesizer in a gel form, increasing the area which can be treated at one time and minimizing the use of photosensitizers, although reaching a higher concentration locally than it would have been achieved following a systemic administration.

It is another object of the present invention to provide a device to deliver the gel photosensitizer, activate the gel and localize the treatment to just the esophagus.

Briefly stated the present invention provides an apparatus and method for treating Barrett's tissue by removal of the mucosa through PhotoDynamic Therapy(PDT). A viscous gel is the medium used to carry the photosensitizer to the treatment site and allow sufficient time to transfer to the tissue. The gel's viscosity allows it to adhere to the tissue for a sufficient amount of time to transfer the photosensitizer or sufficient time for a mechanical device such as an expanding balloon to press the gel into the tissue. The photosensitizer within the gel is activated by the corresponding wavelength of radiation. An extended multi-balloon system limits the area of treatment and localizes the spread of the gel. An endoscope with fiber optics may be used to view the operation. A preferred embodiment of the apparatus contains a catheter with at least two balloons, one to block drainage of the photosensitizer into the stomach and one to limit the height of the treatment area and to press the gel into the tissue. Included in this embodiment is a tube for the delivery of the gel, a tube for cooling purposes or aspiration, an image bundle and a diffuse light source. The apparatus and method may be used to treat various other diseases involving the gastrointestinal diseases of the mucosa. The most salient feature of this invention is the multi-balloon system used to limit the area of treatment, but effect the entire desired area at one time.

The above, and other objects, features and advantages of the present invention will become apparent from the following description read in conjunction with the accompanying drawing, (in which like reference numbers in different drawings designate the same elements.)

BRIEF DESCRIPTION OF FIGURES

FIG. 1—Double Ballooned Catheter With Various Endoscopic Devices

DETAILED DESCRIPTION OF PREFERRED EMBODIMENTS

The mechanism for the delivery of the job must perform a few basic functions. First, the gel must be delivered to the treatment site. The gel can be applied through a catheter as a pre-mixed gel or through a double lumen catheter and mixed at the treatment site. In place of a straight gel, a liquid which is gels after contact with the afflicted surface can serve the same purpose in delivering the photosensitizer to the treatment site.

The conventional application of the photosensitizer through spraying results in a loss of material. The spraying of the photosensitizer to the treatment area is an inefficient method of saturating the tissue in that the liquid will drip off the mucosa into the stomach. This liquid nature of the photosensitizer also creates a problem in controlling the treatment area. Dripping or overspray may cause areas of the esophagus to receive unwanted treatment.

Next after delivery to the site, the gel is prevented from moving beyond the treatment site. Not delimiting the treatment area can lead to treatment of areas not needing treatment. Not preventing dripping into the stomach can also result in waste of the photosensitizer. Delimiting the treatment areas can be done in a number of ways. One way is to use multi-balloon catheters to minimize dripping into the stomach and to define the upper limit of the treatment area. Upper and lower limits of treatments could also be delimited with expanding diaphragm devices through which a catheter could poke through and form a seal.

After delimiting the treatment site and delivering the gel, the gel can then be pressed into the esophageal mucosa to insure that there is an even distribution of medication. A balloon catheter could be used here to press the gel. Several forms of the balloon could be used depending on the viscosity of the gel being used. Balloons may have grooves to allow easier flow through thick gels, have a swirling or vibrating motion to insure more complete even distribution or have ridges to remove excess gel. Alternatively, the gel could be allowed to sit and spread on its own.

A diffuse radiation source is then applied to the areas covered by the gel to activate the photosensitizer. This radiation source may be obtained in many different ways including, for example, laser endoscope with diffusers, chemoluminscence, and radio frequency devices. Electrical and magnetic fields could also serve to improve the transfer of active molecules through the electrical field.

Excess or spent gel can be removed through a vacuum or spent gel may also be allowed to slide into the stomach and be excreted. The procedure can be viewed through fiber optic bundles passed through the catheter. The present invention is further illustrated by the following example, but is not limited thereby.

Preferred Embodiment 1

In a preferred embodiment catheter (106) having multiple lumen through which are fed a double balloon system. Also fed through these lumen, is vacuum tube (104) for removal of excess or spent gel, a lumen for the delivery of the gel (105), a diffuse light source (103) between the balloons for activation of the gel and possibly a lumen for an image bundle (107).

The lower balloon (102) will project beyond the lower esophageal sphincter, inflate and then be retracted to prevent leakage of the gel into the stomach. The gel is delivered to the treatment area through a delivery tube and the upper balloon (101) is used to press the gel in to the mucosa. The diffuse light source (103) activates the photosensitizer.

Having described a preferred embodiment of the invention with reference to the accompanying drawing, it is to be understood that the invention is not limited to the precise embodiments, and that various changes and modifications may be effected therein by skilled in the art without departing from the scope or spirit of the invention as defined in the appended claims.

What is claimed is:

1. An endoscopic multi-lumen catheter, having a body consisting of a distal end and a proximal end, for controlled treatment of diseased mucosa in an organ, said catheter containing channels to deliver components to a treatment area, wherein said components comprise:

an applicator means to deliver a highly viscous fluid composition to said treatment area;

viewing means to monitor application and treatment;

irradiating means;

a first balloon associated with a lumen and positioned near said distal end of said body to prevent said fluid from moving away from said treatment area;

a moveable second balloon positioned toward said proximal end relative to said first balloon, wherein said second balloon functions to define a variable upper limit to said treatment area; and wherein one or more of said components are delivered to said treatment area through a single channel within said multi-lumen catheter.

2. An endoscopic multi-lumen catheter according to claim 1, wherein said moveable second balloon has means for applying and pressing said viscous fluid against said diseased mucosa.

3. An endoscopic multi-lumen catheter according to claim 1, wherein said viewing means comprises a fiber optic image bundle.

4. An endoscopic multi-lumen catheter according to claim 1, wherein said irradiating means comprises at least one optical fiber connected at its proximal end to a source of treatment radiation.

* * * * *